US009499633B2

(12) United States Patent
Litzenburger et al.

(10) Patent No.: US 9,499,633 B2
(45) Date of Patent: Nov. 22, 2016

(54) DABIGATRAN ANTIDOTES

(71) Applicants: Tobias Litzenburger, Mittelbiberach (DE); Herbert Nar, Ochsenhausen (DE); Felix Schiele, Berlin (DE); Daniel Seeliger, Biberach an der Riss (DE); Joanne Van Ryn, Warthausen (DE)

(72) Inventors: Tobias Litzenburger, Mittelbiberach (DE); Herbert Nar, Ochsenhausen (DE); Felix Schiele, Berlin (DE); Daniel Seeliger, Biberach an der Riss (DE); Joanne Van Ryn, Warthausen (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 12 days.

(21) Appl. No.: 14/521,499

(22) Filed: Oct. 23, 2014

(65) Prior Publication Data

US 2015/0118225 A1    Apr. 30, 2015

Related U.S. Application Data

(60) Provisional application No. 61/895,443, filed on Oct. 25, 2013.

(51) Int. Cl.
*A61K 39/395* (2006.01)
*C07K 16/44* (2006.01)

(52) U.S. Cl.
CPC ........... *C07K 16/44* (2013.01); *C07K 2299/00* (2013.01); *C07K 2317/24* (2013.01); *C07K 2317/55* (2013.01); *C07K 2317/565* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | | |
|---|---|---|---|---|
| 8,486,398 B2 * | 7/2013 | Van Ryn | ................ | C07K 16/44 424/133.1 |
| 8,821,871 B2 * | 9/2014 | Van Ryn | ................ | C07K 16/44 424/133.1 |
| 9,034,822 B2 * | 5/2015 | Van Ryn | ................ | C07K 16/44 424/134.1 |

FOREIGN PATENT DOCUMENTS

| | | |
|---|---|---|
| WO | 2011089183 A2 | 7/2011 |
| WO | 2012130834 | 10/2012 |

OTHER PUBLICATIONS

Miyares et al., J Pharm Pract. Dec. 2015;28(6):548-54.*
Pollack et al., N Engl J Med. Aug. 6, 2015;373(6):511-20. doi: 10.1056/NEJMoa1502000. Epub Jun. 22, 2015.*
Schier et al., J Mol Biol. Nov. 8, 1996;263(4):551-67.*
Holliger et al., Nat Biotechnol. Sep. 2005;23(9):1126-36.*
Rudikoff et al., Proc Natl Acad Sci U S A. Mar. 1982;79(6):1979-83.*
Janeway et al., Immunobiology, 3rd ed., Current Biology, 1997, pp. 3:1-3:11.*
Campbell, A., Monoclonal Antibody Technology, Elsevier, 1984, pp. 1-32.*
Schiele et al., Blood. May 2, 2013;121(18):3554-62. doi: 10.1182/blood-2012-11-468207. Epub Mar. 8, 2013.*
Schiele, Blood, vol. 121, No. 18, 2013, p. 554-562.
International Search Report and Written opinion, PCT/ISA 220, mailed Feb. 3, 2015.

* cited by examiner

*Primary Examiner* — Michael Szperka
(74) *Attorney, Agent, or Firm* — Michael P. Morris; Timothy X. Witkowski

(57) ABSTRACT

The present invention relates to antibody molecules against anticoagulants, in particular dabigatran, and their use as antidotes of such anticoagulants.

16 Claims, 5 Drawing Sheets

FIG. 1

```
                                    1                                        40
VH5C   (SEQ ID NO: 8)     (1)  QVQLVQSGAEVKKPGASVKVSCKASGYTFTDYYMHWVRQA
VHFAB6 (SEQ ID NO: 9)     (1)  QVQLVQSGAEVKKPGASVKVSCKASGYTFTDYYMHWVRQA 41                                       80
VH5C   (SEQ ID NO: 8)    (41)  PGQGLEWMGETNPRNGGTTYNEKFKGKATMTRDTSTSTAY
VHFAB6 (SEQ ID NO: 9)    (41)  PGQGLEWMGETNPRNGGTTYNEKFKGKATMTRDTSTSTAY 81                                      119
VH5C   (SEQ ID NO: 8)    (81)  MELSSLRSEDTAVYYCTIGTSGYDYFDYWGQGTLVTVSS
VHFAB6 (SEQ ID NO: 9)    (81)  MELSSLRSEDTAVYYCTIGTSGWDYFDYWGQGTLVTVSS
```

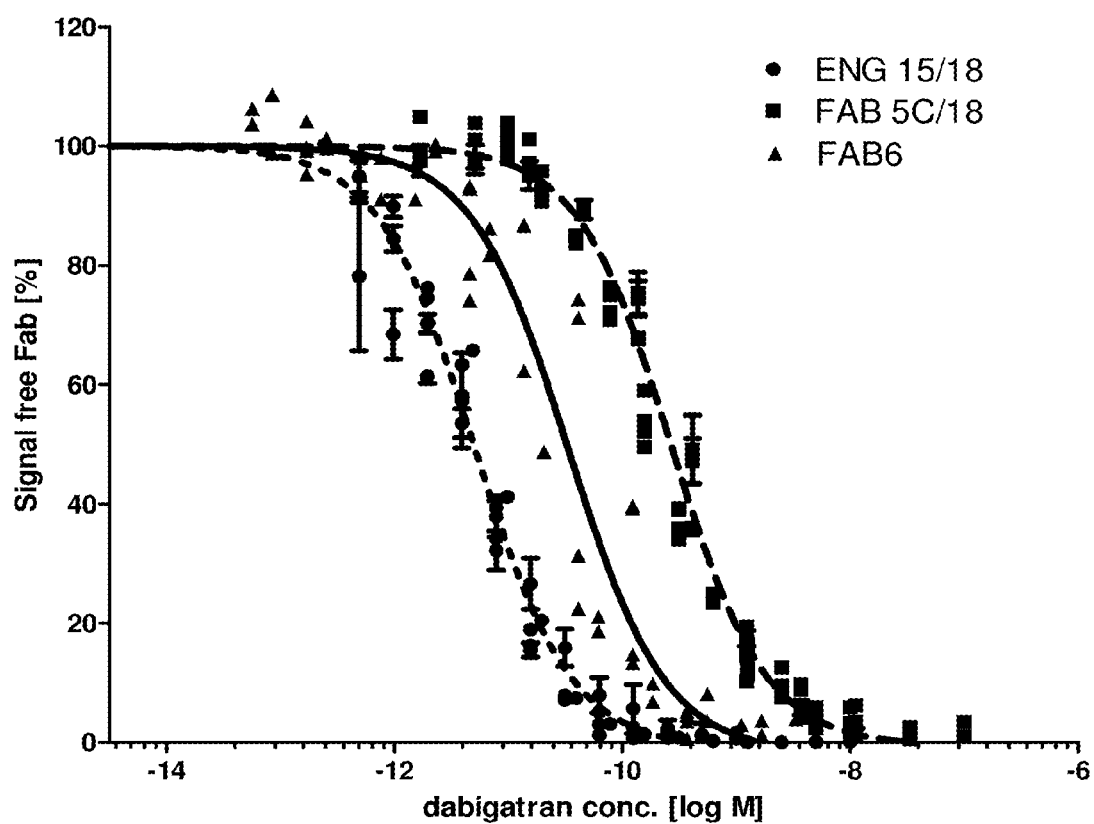

DABIGATRAN ANTIDOTES

SEQUENCE LISTING

The instant application contains a Sequence Listing which has been submitted electronically in ASCII format and is hereby incorporated by reference in its entirety. Said ASCII copy, created on Oct. 22, 2013, is named 01-2960_SL.txt and is 18,732 bytes in size.

TECHNICAL FIELD

The present invention pertains to the field of medicine, in particular to the field of anticoagulant therapy.

BACKGROUND INFORMATION

Anticoagulants are substances that prevent coagulation; that is, they stop blood from clotting. Anticoagulants are widely used in human therapy as a medication for thrombotic disorders, for example primary and secondary prevention of deep vein thrombosis, pulmonary embolism, myocardial infarctions and strokes in those who are predisposed.

An important class of oral anticoagulants acts by antagonizing the effects of vitamin K, for example the coumarins which include warfarin. A second class of compounds inhibit coagulation indirectly via a cofactor such as antithrombin III or heparin cofactor II. This includes several low molecular weight heparin products which catalyse the inhibition of predominantly factor Xa (and to a lesser degree thrombin) via antithrombin III (bemiparin, certoparin, dalteparin, enoxaparin, nadroparin, parnaparin, reviparin, tinzaparin), Smaller chain oligosaccharides (fondaparinux, idraparinux) inhibit only factor Xa via antithrombin III. Heparinoids (danaparoid, sulodexide, dermatan sulfate) act via both cofactors and inhibit both factor Xa and thrombin. A third class represents the direct inhibitors of coagulation. Direct factor Xa inhibitors include apixaban, edoxaban, otamixaban, rivaroxaban, and direct thrombin inhibitors include the bivalent hirudins (bivalirudin, lepirudin, desirudin), and the monovalent compounds argatroban and dabigatran.

As blood clotting is a biological mechanism to stop bleeding, a side effect of anticoagulant therapy may be unwanted bleeding events. It is therefore desirable to provide an antidote to be able to stop such anticoagulant-related bleeding events when they occur (Zikria and Ansell, Current Opinion in Hematology 2009, 16(5): 347-356). One way to achieve this is by neutralizing the activity of the anticoagulant compound present in the patient after administration.

Currently available anticoagulant antidotes are protamine (for neutralization of heparin) and vitamin K for neutralization of vitamin K antagonists like warfarin. Fresh frozen plasma and recombinant factor VIIa have also been used as non-specific antidotes in patients under low molecular weight heparin treatment, suffering from major trauma or severe hemorrhage (Lauritzen, B. et al, Blood, 2005, 607A-608A.). Also reported are protamine fragments (U.S. Pat. No. 6,624,141) and small synthetic peptides (U.S. Pat. No. 6,200,955) as heparin or low molecular weight heparin antidotes; and thrombin muteins (U.S. Pat. No. 6,060,300) as antidotes for thrombin inhibitor. Prothrombin intermediates and derivatives have been reported as antidotes to hirudin and synthetic thrombin inhibitors (U.S. Pat. Nos. 5,817,309 and 6,086,871). For direct factor Xa inhibitors, inactive factor Xa analogs have been proposed as antidotes (WO2009042962). Furthermore, recombinant factor VIIa has been used to reverse the effect of indirect antithrombin III dependent factor Xa inhibitors such as fondaparinux and idraparinux (Bijsterveld, N R et al, Circulation, 2002, 106: 2550-2554; Bijsterveld, N R et al, British J. of Haematology, 2004 (124): 653-658). A review of methods of anticoagulant reversal is provided in Schulman and Bijsterveld, Transfusion Medicine Reviews 2007, 21(1): 37-48.

International patent applications WO 2011/089183 and WO2012/130834 disclose antibody molecules that can bind and neutralize the activity of dabigatran.

There is a need to provide improved antidotes for anticoagulant therapy, and in particular to provide antidotes for direct thrombin inhibitors like dabigatran for which no specific antidotes have been disclosed so far.

BRIEF SUMMARY OF THE INVENTION

In one aspect, the present invention relates to an antibody molecule capable of neutralizing the activity of an anticoagulant.

In a further aspect, the antibody molecule has binding specificity for the anticoagulant.

In a further aspect, the anticoagulant is a direct thrombin inhibitor.

In a further aspect, the anticoagulant is dabigatran.

In another aspect, the present invention relates to an antibody molecule against dabigatran, dabigatran exetilate, and/or an O-acylglucuronide of dabigatran.

In a further aspect, the present invention relates to an antibody molecule against dabigatran, dabigatran exetilate, and/or an O-acylglucuronide of dabigatran with reduced immunogenicity in man.

In a further aspect, the present invention relates to an antibody molecule against dabigatran, dabigatran exetilate, and/or an O-acylglucuronide of dabigatran with improved physicochemical properties, in particular improved solubility in aqueous solvents.

In a further aspect, the present invention relates to an antibody molecule against dabigatran, dabigatran exetilate, and/or an O-acylglucuronide of dabigatran with improved produceability in host cells, in particular resulting in improved production yields.

In a further aspect, the antibody molecule is a polyclonal antibody, a monoclonal antibody, a human antibody, a humanized antibody, a chimeric antibody, a fragment of an antibody, in particular a Fab, Fab', or F(ab')$_2$ fragment, a single chain antibody, in particular a single chain variable fragment (scFv), a domain antibody, a nanobody, a diabody, or a DARPin.

In a further aspect, the present invention relates to an antibody molecule as described above for use in medicine.

In a further aspect, the present invention relates to an antibody molecule as described above for use in the therapy or prevention of side effects of anticoagulant therapy.

In a further aspect, the side effect is a bleeding event.

In a further aspect, the present invention relates to a method of treatment or prevention of side effects of anticoagulant therapy, comprising administering an effective amount of an antibody molecule as described above to a patient in need thereof.

In another aspect, the present invention relates to a kit comprising an antibody molecule as described, together with a container and a label.

BRIEF DESCRIPTION OF THE DRAWINGS

FIG. 1: Sequence alignment of the variable domain of heavy chain 5C (SEQ ID NO: 8) and the variable domain of the heavy chain of FAB6.

FIG. 2: Dabigatran-Fab binding curves. Constant concentrations of Fab were incubated with increasing concentrations of dabigatran. The concentration of free Fab was then determined by capturing the unbound Fab on a dabigatran-biotin conjugate coupled to Neutravidin beads.

DETAILED DESCRIPTION OF THE INVENTION

Figure 3:
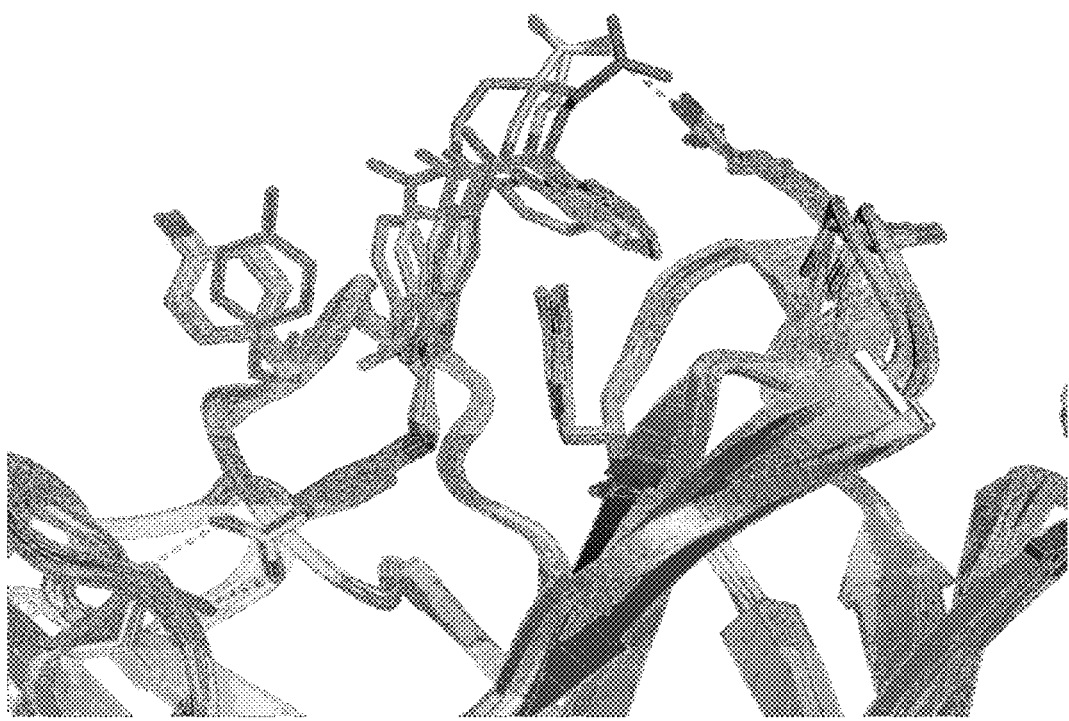
FIG. 3: Structural data: A series of experimentally determined binding modes of dabigatran in complex with FAB5C/18/FAB5C/21 show that dabigatran is tightly bound with its benzamidine moiety in a hydrophobic pocket (lower left in the above figure), whereas the benzimidazole, carboxamide, pyridine and carboxyl moieties show slightly different orientations in the different crystal systems and crystallographically independent promoters, which indicates a certain variability of the positioning of these groups when dabigatran is bound in complex with Fab. The further the latter groups are shifted to the right in the above orientation the better the fit of dabigatran to the right part of the Fab paratope becomes (for instance the 0.11-stacking interactions with Tyr33 to the right of the benzimidazole and the deeper penetration of the pyridine moiety in the pocket between Tyr33 and Arg54), while on the left side either the edge-to-face interaction to Tyr103 is lost or Tyr33 has to break a hydrogen bond of its OH group with Asp33L (Asp33L not shown). Tyr103 is shown in the upper left. Substitution of Tyr103 by Trp103 results in a tighter fit of dabigatran in the binding site with aromatic edge-to-face (Trp103) or face-to-face (Tyr33) interactions of the benzimidazole moiety on both of its sides.
Figure 4:
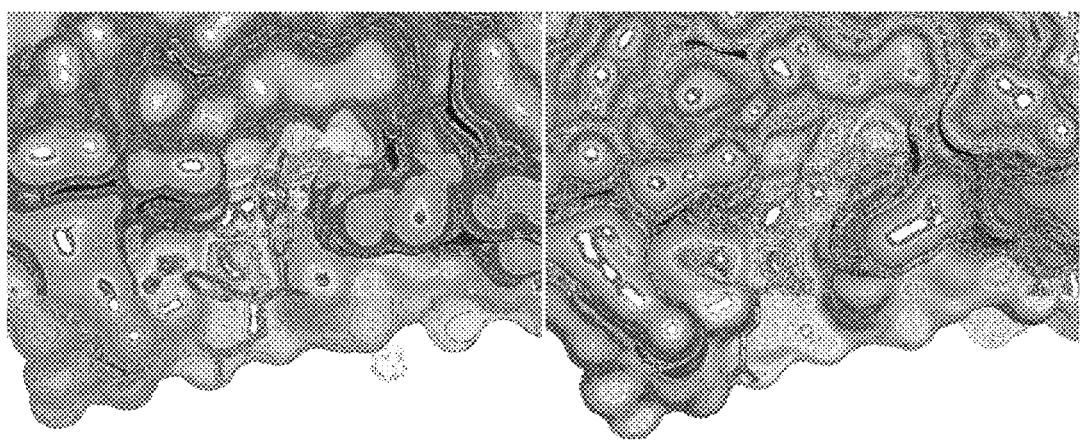
FIG. 4: Structural data: The surface representation shows the improved site occupation of dabigatran in FAB6 (right picture) relative to FAB5C/18 (left).
Figure 5:
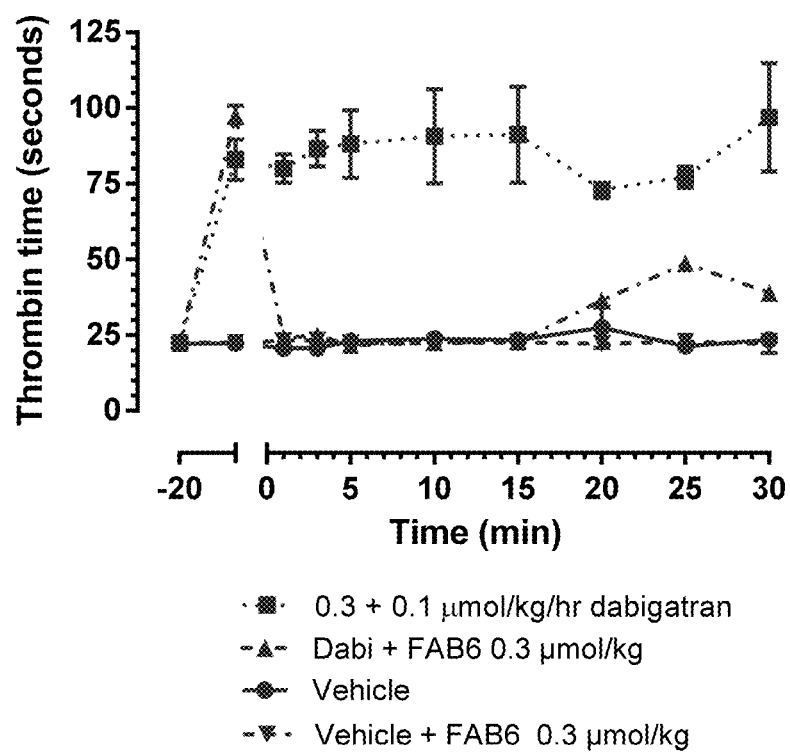
FIG. 5: Neutralization of dabigatran anticoagulant activity by FAB6 after intravenous administration in rats that were pre-treated with a continuous infusion of dabigatran. Anticoagulant activity was measured as the thrombin time using 3 U/ml thrombin. Data represented as mean±SE, n=4-8.

In one aspect, the present invention relates to an antibody molecule capable of neutralizing the activity of dabigatran.

WO 2012/130834 discloses neutralizing anti-dabigatran antibody molecules VH5c/Vk18 and VH5c/Vk21 (herein named FAB 5C/18 and FAB 5C/21, respectively) which have less solvent-exposed hydrophobic surface than the average of known antibodies in the protein data bank. This means that these compounds have an excellent solubility in aqueous media and a low tendency for aggregation, making them particularly suitable for stable drug formulations with high antibody concentrations. Furthermore, these molecules can be produced in very high production titers.

The present invention now provides anti-dabigatran antibody molecules with a single amino acid substitution in the CDR3 of the heavy chain, as compared to the heavy chain variable domain 5C which is shared by the aforementioned antibodies. By this single point mutation (substitution of a tyrosine by a tryptophan residue at position 103 of the heavy chain), the binding affinity could be increased by a factor of 10, while the altered molecules still have the beneficial physicochemical properties (solubility, no aggregation) of their parent molecules.

In the following, references to SEQ ID NO.s. refer to the sequences of Table 1 and the sequence listing which is part of this application, unless indicated otherwise.

In one aspect of the invention, the antibody molecule has binding specificity for dabigatran and comprises heavy chain variable domain with a CDR1 of SEQ ID NO: 1, a CDR2 of SEQ ID NO: 2, and a CDR3 of SEQ ID NO: 4, and a light chain variable domain with a CDR1 of SEQ ID NO: 5, a CDR2 of SEQ ID NO: 6, and a CDR3 of SEQ ID NO: 7.

In another aspect of the invention, the antibody molecule comprises a heavy chain variable domain of SEQ ID NO: 9, and a light chain variable domain of SEQ ID No: 10.

In another aspect of the invention, the antibody molecule comprises a heavy chain variable domain of SEQ ID NO: 9, and a light chain variable domain of SEQ ID No: 11.

In another aspect of the invention, the antibody molecule comprises a heavy chain of SEQ ID NO: 13, and a light chain of SEQ ID No: 14.

In another aspect of the invention, the antibody molecule comprises a heavy chain of SEQ ID NO: 13, and a light chain of SEQ ID No: 15.

In another aspect of the invention, the antibody molecule consists of a heavy chain of SEQ ID NO: 13, and a light chain of SEQ ID No: 14.

Antibodies (also known as immunoglobulins, abbreviated Ig) are gamma globulin proteins that can be found in blood or other bodily fluids of vertebrates, and are used by the immune system to identify and neutralize foreign objects, such as bacteria and viruses. They are typically made of basic structural units—each with two large heavy chains and two small light chains—to form, for example, monomers with one unit, dimers with two units or pentamers with five units. Antibodies can bind, by non-covalent interaction, to other molecules or structures known as antigens. This binding is specific in the sense that an antibody will only bind to a specific structure with high affinity. The unique part of the antigen recognized by an antibody is called an epitope, or antigenic determinant. The part of the antibody binding to the epitope is sometimes called paratope and resides in the so-called variable domain, or variable region (Fv) of the antibody. The variable domain comprises three so-called complementary-determining region (CDR's) spaced apart by framework regions (FR's).

Within the context of this invention, reference to CDR's is based on the definition of Chothia (Chothia and Lesk, J. Mol. Biol. 1987, 196: 901-917), together with Kabat (E. A. Kabat, T. T. Wu, H. Bilofsky, M. Reid-Miller and H. Perry, Sequence of Proteins of Immunological Interest, National Institutes of Health, Bethesda (1983)).

The art has further developed antibodies and made them versatile tools in medicine and technology. Thus, in the context of the present invention the terms "antibody molecule" or "antibody" (used synonymously herein) do not only include antibodies as they may be found in nature, comprising e.g. two light chains and two heavy chains, or just two heavy chains as in camelid species, but furthermore encompasses all molecules comprising at least one paratope with binding specificity to an antigen and structural similarity to a variable domain of an immunoglobulin.

Thus, an antibody molecule according to the invention may be a polyclonal antibody, a monoclonal antibody, a human antibody, a humanized antibody, a chimeric antibody, a fragment of an antibody, in particular a Fv, Fab, Fab', or F(ab')$_2$ fragment, a single chain antibody, in particular a single chain variable fragment (scFv), a Small Modular Immunopharmaceutical (SMIP), a domain antibody, a nanobody, a diabody.

Polyclonal antibodies represent a collection of antibody molecules with different amino acid sequences and may be obtained from the blood of vertebrates after immunization with the antigen by processes well-known in the art.

Monoclonal antibodies (mAb or moAb) are monospecific antibodies that are identical in amino acid sequence. They may be produced by hybridoma technology from a hybrid cell line (called hybridoma) representing a clone of a fusion of a specific antibody-producing B cell with a myeloma (B cell cancer) cell (Kohler G, Milstein C. Continuous cultures of fused cells secreting antibody of predefined specificity. Nature 1975; 256:495-7.). Alternatively, monoclonal antibodies may be produced by recombinant expression in host cells (Norderhaug L, Olafsen T, Michaelsen T E, Sandlie I. (May 1997). "Versatile vectors for transient and stable expression of recombinant antibody molecules in mammalian cells.". J Immunol Methods 204 (1): 77-87; see also below).

For application in man, it is often desirable to reduce immunogenicity of antibodies originally derived from other species, like mouse. This can be done by construction of chimeric antibodies, or by a process called "humanization". In this context, a "chimeric antibody" is understood to be an antibody comprising a sequence part (e.g. a variable domain) derived from one species (e.g. mouse) fused to a sequence part (e.g. the constant domains) derived from a different species (e.g. human). A "humanized antibody" is an antibody comprising a variable domain originally derived from a non-human species, wherein certain amino acids have been mutated to resemble the overall sequence of that variable domain more closely to a sequence of a human variable domain. Methods of chimerisation and -humanization of antibodies are well-known in the art (Billetta R, Lobuglio A F. "Chimeric antibodies". Int Rev Immunol. 1993; 10(2-3):165-76; Riechmann L, Clark M, Waldmann H, Winter G (1988). "Reshaping human antibodies for therapy". *Nature:* 332:323.).

Furthermore, technologies have been developed for creating antibodies based on sequences derived from the human genome, for example by phage display or using transgenic animals (WO 90/05144; D. Marks, H. R. Hoogenboom, T. P. Bonnert, J. McCafferty, A. D. Griffiths and G. Winter (1991) "By-passing immunisation. Human antibodies from V-gene libraries displayed on phage." J. Mol. Biol., 222, 581-597; Knappik et al., J. Mol. Biol. 296: 57-86, 2000; S. Carmen and L. Jermutus, "Concepts in antibody phage display". Briefings in Functional Genomics and Proteomics 2002 1(2):189-203; Lonberg N, Huszar D. "Human antibodies from transgenic mice". Int Rev Immunol. 1995; 13(1):65-93; Bruggemann M, Taussig M J. "Production of human antibody repertoires in transgenic mice". Curr Opin Biotechnol. 1997 August; 8(4):455-8.). Such antibodies are "human antibodies" in the context of the present invention.

Antibody molecules according to the present invention also include fragments of immunoglobulins which retain antigen binding properties, like Fab, Fab', or F(ab')$_2$ fragments. Such fragments may be obtained by fragmentation of immunoglobulins e.g. by proteolytic digestion, or by recombinant expression of such fragments. For example, immunoglobulin digestion can be accomplished by means of routine techniques, e.g. using papain or pepsin (WO 94/29348), or endoproteinase Lys-C (Kleemann, et al, Anal. Chem. 80, 2001-2009, 2008). Papain or Lys-C digestion of antibodies typically produces two identical antigen binding fragments, so-called Fab fragments, each with a single antigen binding site, and a residual Fc fragment. Pepsin treatment yields an F(ab')$_2$. Methods of producing Fab molecules by recombinant expression in host cells are outlined in more detail below.

A number of technologies have been developed for placing variable domains of immunoglobulins, or molecules derived from such variable domains, in a different molecular context. Those should be also considered as "antibody molecules" in accordance with the present invention. In general, these antibody molecules are smaller in size compared to immunoglobulins, and may comprise a single amino acid chain or be composed of several amino acid chains. For example, a single-chain variable fragment (scFv) is a fusion of the variable regions of the heavy and light chains of immunoglobulins, linked together with a short linker, usually serine (S) or glycine (G) (WO 88/01649; WO 91/17271; Huston et al; International Reviews of Immunology, Volume 10, 1993, 195-217). "Single domain antibodies" or "nanobodies" harbour an antigen-binding site in a single Ig-like domain (WO 94/04678; WO 03/050531, Ward et al., Nature. 1989 Oct. 12; 341(6242):544-6; Revets et al., Expert Opin Biol Ther. 5(1):111-24, 2005). One or more single domain antibodies with binding specificity for the same or a different antigen may be linked together. Diabodies are bivalent antibody molecules consisting of two amino acid chains comprising two variable domains (WO 94/13804, Holliger et al., Proc Natl Acad Sci USA. 1993 Jul. 15; 90(14):6444-8). Other examples for antibody-like molecules are immunoglobulin super family antibodies (IgSF; Srinivasan and Roeske, Current Protein Pept. Sci. 2005, 6(2): 185-96). A different concept leads to the so-called Small Modular Immunopharmaceutical (SMIP) which comprises a Fv domain linked to single-chain hinge and effector domains devoid of the constant domain CH1 (WO 02/056910).

The antibody molecule may be fused (as a fusion protein) or otherwise linked (by covalent or non-covalent bonds) to other molecular entities having a desired impact on the properties of the antibody molecule. For example, it may be desirable to improve pharmacokinetic properties of antibody molecules, stability e.g. in body fluids such as blood, in particular in the case of single chain antibodies or domain antibodies. A number of technologies have been developed in this regard, in particular to prolong half-life of such antibody molecules in the circulation, such as pegylation (WO 98/25971; WO 98/48837; WO 2004081026), fusing or otherwise covalently attaching the antibody molecule to another antibody molecule having affinity to a serum protein like albumin (WO 2004041865; WO 2004003019), or expression of the antibody molecule as fusion protein with all or part of a serum protein like albumin or transferrin (WO 01/79258).

In a further aspect, the antibody molecule has binding specificity for the anticoagulant. "Binding specificity" means that the antibody molecule has a significantly higher binding affinity to the anticoagulant than to structurally unrelated molecules.

Affinity is the interaction between a single antigen-binding site on an antibody molecule and a single epitope. It is expressed by the association constant $K_A = k_{ass}/k_{diss}$, or the dissociation constant $K_D = k_{diss}/k_{ass}$.

In one aspect of the invention, the antibody binds to the anticoagulant with an affinity, as determined e.g. by surface plasmon resonance analysis (Malmqvist M., "Surface plasmon resonance for detection and measurement of antibody-antigen affinity and kinetics.", Curr Opin Immunol. 1993 April; 5(2):282-6.), with a $K_D$ value ranging from 0.1 pM to 100 μM, preferably 1 pM to 100 μM, preferably 1 pM to 1 μM. Antibody affinity can also be measured using kinetic exclusion assay (KinExA) technology (Darling, R. J., and Brault P-A., "Kinetic exclusion assay technology: Characterization of Molecular Interactions." ASSAY and Drug Development Technologies. 2004, Dec. 2(6): 647-657).

The binding affinity of an antibody molecule may be enhanced by a process known as affinity maturation (Marks et al., 1992, Biotechnology 10:779-783; Barbas, et al., 1994, Proc. Nat. Acad. Sci, USA 91:3809-3813; Shier et al., 1995, Gene 169:147-155). Affinity matured antibodies are therefore also embraced in the present invention.

In a further aspect of the invention, the antibody molecule is capable of neutralizing the activity of the anticoagulant.

Dabigatran is known from WO 98/37075, which discloses compounds with a thrombin-inhibiting effect and the effect of prolonging the thrombin time, under the name 1-Methyl-2-[N-(4-amidinophenyl)-aminomethyl]-benzimidazol-5-yl-carboxylic acid-N-(2-pyridyl)-N-(2-hydroxycarbonylethyl)-amide. See also Hauel et al. J Med Chem 2002, 45 (9): 1757-66.

Dabigatran is applied as a prodrug of formula (III):

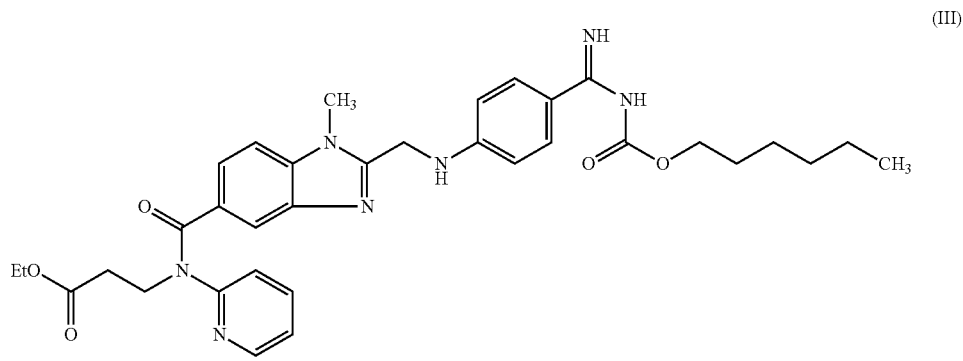 [SMILES: CCCCCCOC(=O)NC(=N)c1ccc(NCc2nc3cc(C(=O)N(CCC(=O)OCC)c4ccccn4)ccc3n2C)cc1]

That is, upon binding to the antibody molecule, the anticoagulant is no longer able to exert its anticoagulant activity, or exerts this activity at a significantly decreased magnitude. Preferably, the anticoagulant activity is decreased at least 2 fold, 5 fold, 10 fold, or 100 fold upon antibody binding, as determined in an activity assay which is appropriate for the anticoagulant at issue, particularly a clotting assay that is sensitive to thrombin, such as the ecarin clotting time or the thrombin clotting time (H. Bounameaux, Marbet G A, Lammle B, et al. "Monitoring of heparin treatment. Comparison of thrombin time, activated partial thromboplastin time, and plasma heparin concentration, and analysis of the behaviour of antithrombin III". American Journal of Clinical Pathology 1980 74(1): 68-72).

For manufacturing the antibody molecules of the invention, the skilled artisan may choose from a variety of methods well known in the art (Norderhaug et al., J Immunol Methods 1997, 204 (1): 77-87; Kipriyanow and Le Gall, Molecular Biotechnology 26: 39-60, 2004; Shukla et al., 2007, J. Chromatography B, 848(1): 28-39).

A preferred anticoagulant in the context of the present invention is dabigatran (CAS 211914-51-1, N-[2-(4-Amidinophenylaminomethyl)-1-methyl-1H-benzimidazol-5-yl-carbonyl]-N-(2-pyridyl)-beta-alanine) having the chemical formula (II):

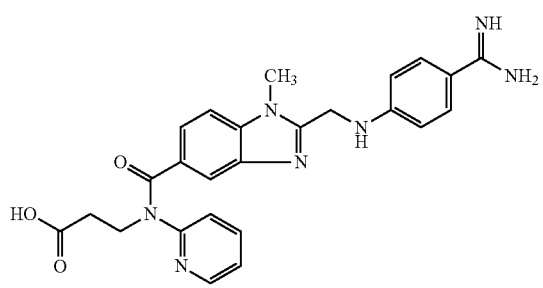

The compound of formula III (named dabigatran etexilate, CAS 211915-06-9; ethyl 3-[(2-{[4-(hexyloxycarbonylamino-imino-methyl)-phenylamino]-methyl}-1-methyl-1H-benzimidazole-5-carbonyl)-pyridin-2-yl-amino] propionate) is converted into the active compound (II) after entering the body. A preferred polymorph of dabigatran etexilate is dabigatran etexilate mesylate.

The main indications for dabigatran are the post-operative prevention of deep-vein thrombosis, the treatment of established deep vein thrombosis and the prevention of strokes in patients with atrial fibrillation (Eriksson et al., Lancet 2007, 370 (9591): 949-56; Schulman S et al, N Engl J Med 2009, 361 (24): 2342-52; Connolly S et al., N Engl J Med 2009, 361 (12): 1139-51; Wallentin et al., Lancet 2010, 376 (9745): 975-983).

In the human body, glucuronidation of the carboxylate moiety is the major human metabolic pathway of dabigatran (Ebner et al., Drug Metab. Dispos. 2010, 38(9):1567-75). It results in the formation of the 1-O-acylglucuronide (beta anomer). The 1-O-acylglucuronide, in addition to minor hydrolysis to the aglycon, may undergo nonenzymatic acyl migration in aqueous solution, resulting in the formation of the 2-O—, 3-O-, and 4-O-acylglucuronides. Experiments with the purified 1-O-acylglucuronide and its isomeric rearrangement products revealed equipotent prolongation of the activated partial thromboplastin time compared with dabigatran.

In another aspect of the invention, the antibody molecule binds both to dabigatran and dabigatran etexilate.

In another aspect of the invention, the antibody molecule binds both to dabigatran and O-acylglucuronides of dabigatran, in particular the 1-O-acylglucuronide of dabigatran.

In another aspect of the invention, the antibody molecule binds furthermore to the 2-O-, 3-O-, and 4-O-acylglucuronides of dabigatran.

In another aspect of the invention, the antibody molecule is capable of neutralizing the activity of dabigatran and O-acylglucuronides of dabigatran, in particular the 1-O-acylglucuronide of dabigatran.

In another aspect of the invention, the antibody molecule is a polyclonal antibody, a monoclonal antibody, a human antibody, a humanized antibody, a chimeric antibody, a fragment of an antibody, in particular a Fab, Fab', or F(ab')$_2$ fragment, a single chain antibody, in particular a single chain variable fragment (scFv), a Small Modular Immunopharmaceutical (SMIP), a domain antibody, a nanobody, a diabody, or a Designed Ankyrin Repeat Protein (DARPin).

In another aspect of the invention, the antibody molecule as herein described is for use in medicine.

In another aspect of the invention, the antibody molecule as herein described is for use in the therapy or prevention of side effects of anticoagulant therapy, and/or for reversal of an overdosing of an anticoagulant. In one aspect, the side effect is a bleeding event.

In another aspect, the invention relates to a method of treatment or prevention of side effects of anticoagulant therapy, or of an overdosing event in anticoagulant therapy, comprising administering an effective amount of an antibody molecule of any one of the preceding claims to a patient in need thereof.

In another aspect, the invention relates to a method of manufacturing an antibody molecule as described herein, comprising providing a host cell comprising one or more nucleic acids encoding said antibody molecule in functional association with an expression control sequence, cultivating said host cell, and recovering the antibody molecule from the cell culture.

In another aspect, present invention relates to a kit comprising an antibody molecule as described, or a pharmaceutical composition thereof.

In another aspect, the present invention relates to a kit comprising: an antibody molecule as described, or a pharmaceutical composition thereof; a container; and a label.

In another aspect, the present invention relates to a kit comprising an antibody molecule as described, and dabigatran, dabigatran etexilate, a prodrug of dabigatran or a pharmaceutically acceptable salt thereof.

In another aspect, the present invention relates to a method for neutralizing or partially neutralizing dabigatran or 1-O-acylglucuronide of dabigatran in a patient being treated with dabigatran, dabigatran etexilate, a prodrug of dabigatran or a pharmaceutically acceptable salt thereof, comprising administering an antibody molecule as described herein, or a pharmaceutical composition thereof.

In another aspect, the present invention relates to a method for neutralizing or partially neutralizing dabigatran or 1-O-acylglucuronide of dabigatran in a patient comprising:
(a) confirming that a patient was being treated with dabigatran, dabigatran etexilate, a prodrug of dabigatran or a pharmaceutically acceptable salt thereof, and the amount that was taken by the patient;
(b) neutralizing dabigatran or 1-O-acylglucuronide with an antibody molecule as described herein prior to performing a clotting or coagulation test or assay wherein dabigatran or the 1-O-acylglucuronide of dabigatran would interfere with the accurate read out of the test or assay results;
(c) performing the clotting or coagulation test or assay on a sample taken from the patient to determine the level of clot formation without dabigatran or 1-O-acylglucuronide of dabigatran present; and
(d) adjusting an amount of dabigatran, dabigatran etexilate, a prodrug of dabigatran or a pharmaceutically acceptable salt thereof administered to the patient in order to achieve the appropriate balance between clot formation and degradation in a patient.

In another aspect, the present invention relates to a method for reducing the concentration of dabigatran or 1-O-acylglucuronide of dabigatran in plasma of a patient being treated with dabigatran, dabigatran etexilate, a prodrug of dabigatran or a pharmaceutically acceptable salt thereof, comprising the step of administering a an antibody molecule as described herein to the patient.

In another aspect, the present invention relates to a method of reversal of the anticoagulant effect of dabigatran or 1-O-acylglucuronide of dabigatran in a patient being treated with dabigatran, dabigatran etexilate, a prodrug of dabigatran or a pharmaceutically acceptable salt thereof, wherein the patient either has major bleeding considered life-threatening or leading to hemodynamic compromise, or wherein the patient requires emergency medical procedures, comprising the step of administering an antibody molecule as described herein to the patient.

Another aspect of the invention is an antibody molecule as described before for use in a patient being treated with dabigatran, dabigatran etexilate, a prodrug of dabigatran or a pharmaceutically acceptable salt thereof, wherein the patient either has major bleeding considered life-threatening or leading to hemodynamic compromise, or wherein the patient requires emergency medical procedures.

In certain aspects, the invention concerns antibodies against dabigatran which have a high solubility in aqueous media and a low tendency of aggregation.

In another aspect of the invention, the antibody molecule is a scFv molecule. In this format, the variable domains disclosed herein may be fused to each other with a suitable linker peptide. The construct may comprise these elements in the order, from N terminus to C terminus, (heavy chain variable domain)-(linker peptide)-(light chain variable domain), or (light chain variable domain)-(linker peptide)-(heavy chain variable domain).

Processes are known in the art which allow recombinant expression of nucleic acids encoding sFv constructs in host cells (like *E. coli, Pichia pastoris*, or mammalian cell lines, e.g. CHO or NS0), yielding functional scFv molecules (see e.g. Rippmann et al., Applied and Environmental Microbiology 1998, 64(12): 4862-4869; Yamawaki et al., J. Biosci. Bioeng. 2007, 104(5): 403-407; Sonoda et al., Protein Expr. Purif. 2010, 70(2): 248-253).

In particular, the scFv antibody molecules of the invention can be produced as follows. The constructs can be expressed in different *E. coli* strains like W3110, TG1, BL21, BL21 (DE3), HMS174, HMS174(DE3), MM294 under control of an inducible promoter. This promoter can be chosen from lacUV5, tac, T7, trp, trc, T5, araB. The cultivation media are preferably fully defined according to Wilms et al., 2001 (Wilms et al., Biotechnology and Bioengineering 2001, 73(2): 95-103), DeLisa et al., 1999 (DeLisa et al., Biotechnology and Bioengineering 1999, 65(1): 54-64) or equivalent. However, supplementation of the batch medium and/or feed medium with amino acids such as isoleucine, leucine, lysine, methionine, phenylalanine, threonine, tryptophan and valine or complex media components such as soy peptone or yeast extract may be beneficial. The process for fermentation is performed in a fed-batch mode. Conditions: Temperature 20-40° C., pH 5.5-7.5, DO is kept above 20%. After consumption of the initial carbon source the culture is fed with the feed media stated above (or equivalent). When a dry cell weight of 40 to 100 g/L is reached in the fermenter, the culture is induced with an appropriate inducer corresponding to the used promoter system (e.g. IPTG, lactose, arabinose). The induction can either be performed as a pulsed full induction or as a partial induction by feeding the respective inducer into the fermenter over a prolonged time or a combination thereof. The production phase should last 4 hours at least. The cells are recovered by centrifugation in bowl centrifuges, tubular bowl centrifuges or disc stack centrifuges, the culture supernatant is discarded.

The E. coli cell mass is resuspended in 4- to 8-fold amount of lysis buffer (phosphate or Tris buffer, pH 7-8.5). Cell lysis is preferably performed by high pressure homogenization followed by recovery of the pellet by centrifugation in bowl, tubular bowl or disc stack centrifuges. Pellet containing scFv inclusion bodies is washed 2-3 times with 20 mM Tris, 150 mM NaCl, 5 mM EDTA, 2 M Urea, 0.5% Triton X-100, pH 8.0 followed by two wash steps using 20 mM Tris, 150 mM NaCl, 5 mM EDTA, pH 8.0. scFv inclusion bodies are finally recovered by centrifugation in bowl, tubular bowl or disc stack centrifuges. Solubilisation of scFv inclusion bodies can be performed in 100 mM Glycine/NaOH, 5 mM EDTA, 20 mM dithiothreitol, pH 9.5-10.5 containing chaotropic agents such as 6 M Guanidine-HCl or 8-10 mM Urea. After incubation for 30-60 minutes solution is centrifuged and supernatant containing the target protein recovered for subsequent refolding. Refolding is preferably performed in fed batch mode by diluting the protein solution 1:10-1:50 in refolding buffer to a final protein concentration of 0.1-0.5 mg/ml. Refolding buffer can contain 50-100 mM Tris and/or 50-100 mM Glycine, 50-150 mM NaCl, 1-3 M urea, 0.5-1 M arginine, 2-6 mM of redox system such as e.g. cytein/cystine or oxidized/reduced glutathione, pH 9.5-10.5. After incubation for 24-72 h at 4° C. refolding solution is optionally filtrated using a 0.22 μm filter, diluted and pH adjusted to pH 7.0-8.0. Protein is separated via cation exchange chromatography in binding mode (e.g. Toyopearl GigaCap S-650M, SP Sepharose FF or S HyperCel™) at pH 7.0-8.5. Elution is performed by a linear increasing NaCl gradient. Fractions containing the target protein are pooled and subsequently separated on anion exchange column in non-binding mode (e.g. Toyopearl GigaCap Q-650M, Q-Sepharose FF, Q HyperCel™) followed by a cation exchange polishing step (eg. SP Sepharose HP). Fractions containing the target protein with a purity level of minimally 90% are pooled and formulated by diafiltration or size exclusion chromatography in PBS. Identity and product quality of the produced scFv molecule are analysed by reducing SDS-PAGE where the scFv can be detected in one major band of approx. 26 kDa. Further assays for characterization of the scFv include mass spectrometry, RP-HPLC and SE-HPLC.

In another aspect of the invention, the antibody molecule is a Fab molecule. In that format, the variable domains disclosed above may each be fused to an immunoglobulin constant domain, preferably of human origin. Thus, the heavy chain variable domain may be fused to a $CH_1$ domain (a so-called Fd fragment), and the light chain variable domain may be fused to a CL domain.

Nucleic acids encoding Fab constructs may be used to express such heavy and light chains in host cells, like E. coli, Pichia pastoris, or mammalian cell lines (e.g. CHO, or NS0). Processes are known in the art which allow proper folding, association, and disulfide bonding of these chains into functional Fab molecules comprising a Fd fragment and a light chain (Burtet et al., J. Biochem. 2007, 142(6), 665-669; Ning et al., Biochem. Mol. Biol. 2005, 38: 204-299; Quintero-Hernandez et al., Mol. Immunol. 2007, 44: 1307-1315; Willems et al. J. Chromatogr. B. Analyt. Technol. Biomed. Life Sci. 2003; 786:161-176.).

In particular, Fab molecules of the invention can be produced in CHO cells as follows. CHO-DG44 cells (Urlaub, G., Kas, E., Carothers, A. M., and Chasin, L. A. (1983). Deletion of the diploid dihydrofolate reductase locus from cultured mammalian cells. Cell 33, 405-412.) growing in suspension in serum-free medium are transfected with expression constructs encoding heavy and light chain of the Fab molecule using Lipofectamine™ and Plus™ reagent (Invitrogen) according to the manufacturer's instructions. After 48 hours, the cells are subjected to selection in medium containing 200 μg/mL of the antibiotic G418 and without hypoxanthine and thymidine to generate stably transfected cell populations. These stable transfectants are subsequently subjected to gene amplification by adding methotrexate (MTX) in increasing concentrations (up to 100 or 400 nM) into the culture medium. Once the cells have adapted, they are subjected to fed-batch fermentations over 10 to 11 days to produce Fab protein material.

Suspension cultures of CHO-DG44 cells and stable transfectants thereof are incubated in chemically defined, serum-free cultivation media. Seed stock cultures are sub-cultivated every 2-3 days with seeding densities of $3 \times 10^5 - 2 \times 10^5$ cells/mL respectively. Cells are grown in shake flasks in Multitron HT incubators (Infors) at 5% $CO_2$, 37° C. and 120 rpm. For fed-batch experiments, cells are seeded at $3 \times 10^5$ cells/mL into shake flasks in BI-proprietary production medium without antibiotics or MTX. The cultures are agitated at 120 rpm in 37° C. and 5% $CO_2$ which is later reduced to 2% as cell numbers increase. Culture parameters including cell count, viability, pH, glucose and lactate concentrations are determined daily and pH is adjusted to pH 7.0 using carbonate as needed. BI-proprietary feed solution is added every 24 hrs. Samples from the supernatant are taken at different time points to determine the Fab product concentration by ELISA. After 10 to 11 days, the cell culture fluid is harvested by centrifugation and transferred to the purification labs.

The Fab molecule is purified from the supernatant of the fed-batch cultures by means of chromatography and filtration. As primary capture step affinity chromatography, e.g. Protein G or Protein L, are applied. Alternatively, in case of low binding affinities and capacities, the Fab is captured by cation exchange chromatography (CEX) exploiting the pI of the molecule. Host cell proteins and contaminants, e.g. DNA or viruses, are removed by additional orthogonal purification steps.

Identity and product quality of the produced Fab molecule are analysed by electrophoretic methods, e.g. SDS-PAGE, by which Fab can be detected as one major band of approx. 50 kDa. Further assays for characterization of the Fab product include mass spectrometry, isoelectric focusing and size exclusion chromatography. Binding activity is followed by BIAcore analysis.

Quantification of Fab or full-length IgG molecules in the supernatant of the cell cultures is performed via sandwich enzyme linked immunosorbent assay (ELISA). The full-length IgG can be detected using antibodies raised against human-Fc fragment (Jackson Immuno Research Laboratories) and human kappa light chain (peroxidase-conjugated, Sigma). The Fab fragment is immobilized by goat polyclonal anti-Human IgG (H and L, Novus) and detected by sheep polyclonal antibodies raised against human IgG (peroxidase-conjugated, The Binding Site).

Fab molecules can also be generated from full-length antibody molecules by enzymatic cleavage. The advantage of this approach is that platform processes for robust and efficient fermentation and purification are applicable which are amenable for up-scaling and high yields at the desired product quality. For purification affinity chromatography using a recombinant Protein A resin can be used as primary capture step which usually results in high purities.

For this purpose, the heavy chain encoding Fab sequences are fused to the Fc-region of a human IgG antibody molecule. The resulting expression constructs are then transfected into CHO-DG44 cells growing in suspension in serum-free medium using lipofection. After 48 hours, the cells are subjected to selection in medium containing 200 μg/mL of the antibiotic G418 and without hypoxanthine and thymidine to generate stably transfected cell populations. These stable transfectants are subsequently subjected to gene amplification by adding methotrexate (MTX) in increasing concentrations (up to 100 or 400 nM) into the culture medium. Once the cells have adapted, they are subjected to fed-batch fermentations over 10 to 11 days to produce IgG protein material.

The IgG protein is purified from the culture supernatant by using recombinant Protein A-affinity chromatography. To obtain the desired neutralizing Fab fragment the full-length IgG is then incubated in the presence of papain which cleaves the IgG within the hinge region, thereby releasing two Fab fragments and the Fc-moiety.

The Fab molecule is isolated by affinity chromatography, e.g. Protein G or Protein L. Alternatively, in case of low binding affinities and capacities, the Fab is captured by cation exchange chromatography (CEX) exploiting the pI of the molecule. Host cell proteins and contaminants, e.g. Papain, DNA or viruses, are removed by additional orthogonal purification steps.

In another aspect of the invention, the antibody molecule is an amino acid sequence variant of an antibody molecule as described herein.

Amino acid sequence variants of antibodies can be prepared by introducing appropriate nucleotide changes into the antibody DNA, or by peptide synthesis. Such variants include, for example, deletions from, and/or insertions into and/or substitutions of, residues within the amino acid sequences of the antibodies of the examples herein. Any combination of deletions, insertions, and substitutions is made to arrive at the final construct, provided that the final construct possesses the desired characteristics. The amino acid changes also may alter post-translational processes of the humanized or variant antibody, such as changing the number or position of glycosylation sites.

A useful method for identification of certain residues or regions of the antibody that are preferred locations for mutagenesis is called "alanine scanning mutagenesis," as described by Cunningham and Wells (Science, 244:1081-1085 (1989)). Here, a residue or group of target residues are identified (e.g., charged residues such as arg, asp, his, lys, and glu) and replaced by a neutral or negatively charged amino acid (typically alanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, alanine scanning or random mutagenesis is conducted at the target codon or region and the expressed antibody variants are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody fused to an epitope tag. Other insertional variants of the antibody molecule include a fusion to the N- or C-terminus of the antibody of an enzyme or a polypeptide which increases the serum half-life of the antibody.

Another type of variant is an amino acid substitution variant. These variants have at least one amino acid residue in the antibody molecule removed and a different residue inserted in its place. The sites of greatest interest for substitutional mutagenesis include the hypervariable regions, but FR alterations are also contemplated. Conservative substitutions are shown in the Table below under the heading of "preferred substitutions". If such substitutions result in a change in biological activity, then more substantial changes, denominated "exemplary substitutions", or as further described below in reference to amino acid classes, may be introduced and the products screened.

| Original Residue | Exemplary Substitutions | Preferred Substitutions |
| --- | --- | --- |
| Ala (A) | val; leu; ile | val |
| Arg (R) | lys; gln; asn | lys |
| Asn (N) | gln; his; asp, lys; arg | gln |
| Asp (D) | glu; asn | glu |
| Cys (C) | ser; ala | ser |
| Gln (Q) | asn; glu | asn |
| Glu (E) | asp; gln | asp |
| Gly (G) | ala | ala |
| His (H) | arg; asn; gln; lys; | arg |
| Ile (I) | leu; val; met; ala; phe; norleucine | leu |
| Leu (L) | ile; norleucine; val; met; ala; phe | ile |
| Lys (K) | arg; gln; asn | arg |
| Met (M) | leu; phe; ile | leu |
| Phe (F) | tyr; leu; val; ile; ala; | tyr |
| Pro (P) | ala | ala |
| Ser (S) | thr | thr |
| Thr (T) | ser | ser |
| Trp (W) | tyr; phe | tyr |
| Tyr (Y) | phe; trp; thr; ser | phe |
| Val (V) | leu; ile; met; phe ala; norleucine; | leu |

In protein chemistry, it is generally accepted that the biological properties of the antibody can be accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gin, his, lys, arg;
(5) residues that influence chain orientation: gly, pro; and
(6) aromatic: trp, tyr, phe.

Non-conservative substitutions will entail exchanging a member of one of these classes for another class.

Any cysteine residue not involved in maintaining the proper conformation of the humanized or variant antibody also may be substituted, generally with serine, to improve the oxidative stability of the molecule, prevent aberrant crosslinking, or provide for established points of conjugation to a cytotoxic or cytostatic compound. Conversely, cysteine bond(s) may be added to the antibody to improve its stability (particularly where the antibody is an antibody fragment such as an Fv fragment).

A type of substitutional variant involves substituting one or more hypervariable region residues of a parent antibody (e.g., a humanized or human antibody). Generally, the resulting variant(s) selected for further development will have improved biological properties relative to the parent antibody from which they are generated. A convenient way for generating such substitutional variants is affinity maturation using phage display. Briefly, several hypervariable region sites (e.g., 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g., binding affinity). In order to identify candidate hypervariable region sites for modification, alanine scanning mutagenesis can be performed to identify hypervariable region residues contributing significantly to antigen binding. Alternatively, or in addition, it may be beneficial to analyse a crystal structure of the antigen-antibody complex to identify contact points between the antibody and human Dabigatran. Such contact residues and neighbouring residues are candidates for substitution according to the techniques elaborated herein. Once such variants are generated, the panel of variants is subjected to screening as described herein and antibodies with superior properties in one or more relevant assays may be selected for further development.

Another type of amino acid variant of the antibody alters the original glycosylation pattern of the antibody. By "altering" is meant deleting one or more carbohydrate moieties found in the antibody, and/or adding one or more glycosylation sites that are not present in the antibody.

In some embodiments, it may be desirable to modify the antibodies of the invention to add glycosylations sites. Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used. Thus, in order to glycosylate a given protein, e.g., an antibody, the amino acid sequence of the protein is engineered to contain one or more of the above-described tripeptide sequences (for N-linked glycosylation sites). The alteration may also be made by the addition of, or substitution by, one or more serine or threonine residues to the sequence of the original antibody (for O-linked glycosylation sites).

Nucleic acid molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of an antibody molecule as described herein. As outlined above, the antigen of the antibody molecule of the invention is an anticoagulant. The antigen is used to generate the antibody molecule, either by immunization of an animal, or by selecting antibody sequences from sequence libraries, as with phage display methods.

Immunization protocols for animals are well-known in the art. To achieve a proper immune response, it may be necessary to combine the antigen with an adjuvant, like aluminium phosphate, aluminium hydroxide, squalene, or Freund's complete/incomplete adjuvant. The antigens in the context of the present invention, like dabigatran, are mostly comparably small organic molecules, which sometimes do not stimulate antibody formation upon administration to an animal. It may therefore be necessary to attach the antigen to a macromolecule, as a hapten.

In a further aspect, the present invention relates to a pharmaceutical composition comprising an antibody molecule as described before, and a pharmaceutical carrier.

To be used in therapy, the antibody molecule is included into pharmaceutical compositions appropriate to facilitate administration to animals or humans. Typical formulations of the antibody molecule can be prepared by mixing the antibody molecule with physiologically acceptable carriers, excipients or stabilizers, in the form of lyophilized or otherwise dried formulations or aqueous solutions or aqueous or non-aqueous suspensions. Carriers, excipients, modifiers or stabilizers are nontoxic at the dosages and concentrations employed. They include buffer systems such as phosphate, citrate, acetate and other anorganic or organic acids and their salts; antioxidants including ascorbic acid and methionine; preservatives such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); proteins, such as serum albumin, gelatin, or immunoglobulins; hydrophilic polymers such as polyvinylpyrrolidone or polyethylene glycol (PEG); amino acids such as glycine, glutamine, asparagine, histidine, arginine, or lysine; monosaccharides, disaccharides, oligosaccharides or polysaccharides and other carbohydrates including glucose, mannose, sucrose, trehalose, dextrins or dextrans; chelating agents such as EDTA; sugar alcohols such as, mannitol or sorbitol; salt-forming counter-ions such as sodium; metal complexes (e.g., Zn-protein complexes); and/or ionic or non-ionic surfactants such as TWEEN™ (polysorbates), PLURONICS™ or fatty acid esters, fatty acid ethers or sugar esters. Also organic solvents can be contained in the antibody formulation such as ethanol or isopropanol. The excipients may also have a release-modifying or absorption-modifying function.

In one aspect, the pharmaceutical composition comprises the antibody molecule in an aqueous, buffered solution at a concentration of 10-20 mg/ml, or a lyophilisate made from such a solution.

The preferred mode of application is parenteral, by infusion or injection (intravenous, intramuscular, subcutaneous, intraperitoneal, intradermal), but other modes of application such as by inhalation, transdermal, intranasal, buccal, oral, may also be applicable.

In a preferred embodiment, the antibody molecule against dabigatran as herein described.

Is used to neutralize the anticoagulant activity of dabigatran, dabigatran etexilate, and/or 1-O-acylglucuronide.

Preferably, the concentration of dabigatran or 1-O-acylglucuronide of dabigatran in plasma is greater than 0 nM but less than 1000 μM and wherein the reversal agent used to neutralize the activity of dabigatran or 1-O-acylglucuronide is present in a stoichiometric amount of dabigatran or 1-O-acylglucuronide of dabigatran to reversal agent.

In a further aspect, the concentration of dabigatran or 1-O-acylglucuronide of dabigatran in plasma is greater than 0 nM but less than 1000 μM, and wherein the reversal agent used to neutralize the activity of dabigatran or 1-O-acylglucuronide is present in a molar ratio of between 1:1 and 1:100 of dabigatran or 1-O-acylglucuronide of dabigatran to reversal agent.

In a further aspect, the concentration of dabigatran or 1-O-acylglucuronide of dabigatran in plasma is between 30 nM and 1000 μM, and wherein the reversal agent used to neutralize the activity of dabigatran or 1-O-acylglucuronide is present in a ratio of between 30 nM and 1000 μM of dabigatran or 1-O-acylglucuronide of dabigatran to reversal agent.

In another aspect, the present invention relates to a method for reversing or reducing the activity of dabigatran or 1-O-acylglucuronide of dabigatran in a patient experiencing bleeding or at risk for bleeding due to an impaired clotting ability or trauma, comprising the steps of:

(a) determining the amount of dabigatran or 1-O-acylglucuronide of dabigatran present in the patient;
(b) administering an effective amount of an antibody as herein described to reverse or reduce the activity of dabigatran or 1-O-acylglucuronide of dabigatran determined in the patient; and
(c) monitoring a thrombin clotting time or similar clotting test of the patient to ensure a reversal or reduction in activity of dabigatran or 1-O-acylglucuronide of dabigatran has been reached.

In a preferred aspect, the reversal of activity of dabigatran or 1-O-acylglucuronide of dabigatran is 100%. In a further preferred aspect, the reduction of activity of dabigatran or 1-O-acylglucuronide of dabigatran is between 10 and 99% of dabigatran or 1-O-acylglucuronide of dabigatran in the patient.

The "therapeutically effective amount" of the antibody to be administered is the minimum amount necessary to prevent, ameliorate, or treat the side effects of anticoagulant therapy, in particular the minimum amount which is effective to stop bleeding. This can be achieved with stoichiometric amounts of antibody molecule.

Dabigatran, for example, may achieve a plasma concentration in the magnitude of 200 nM when given at the recommended dose. When a monovalent antibody molecule with a molecular weight of ca. 50 kD is used, neutralization may be achieved for example at a dose of about 1 mg/kg, when given intravenously as a bolus. In another embodiment, the dose of a Fab molecule applied to a human patient may be 50-1000 mg per application, for example 100, 200, 500, 750, or 1000 mg. Depending on the situation, e.g. when dabigatran has been overdosed in a patient, it may be adequate to apply an even higher dose, e.g. 1250, 1500, 1750 or 2000 mg per application. The appropriate dose may be different, depending on the type and dose of anticoagulant administered; the time elapsed since such administration, the nature of the antigen molecule, the condition of the patient, and other factors. The skilled expert knows methods to establish doses which are both therapeutically effective and safe.

In a further aspect, the present invention relates to an antibody molecule as herein described with binding affinity to dabigatran and/or dabigatran etexilate. Preferably, the antibody molecule binds to the dabigatran and/or dabigatran etexilate with an affinity, as determined e.g. by surface plasmon resonance analysis (Malmqvist M., "Surface plasmon resonance for detection and measurement of antibody-antigen affinity and kinetics. "Curr Opin Immunol. 1993 April; 5(2):282-6.) or kinetic exclusion assay (KinExA) technology (Darling, R. J., and Brault P-A., "Kinetic exclusion assay technology: Characterization of Molecular Interactions." ASSAY and Drug Development Technologies. 2004, Dec. 2(6): 647-657), with a $K_D$ value ranging from 0.1 pM to 100 μM, preferably 1 pM to 100 μM, more preferably 1 pM to 1 μM.

The antibody molecules of the invention can also be used for analytical and diagnostic procedures, for example to determine antigen concentration in samples such as plasma, serum, or other body fluids. For example, the antigen molecules may be used in an enzyme-linked immunoadsorbent assay (ELISA), like those described in the examples. Thus, in a further aspect, the present invention relates to analytical and diagnostic kits comprising antibody molecules a described herein, and to respective analytical and diagnostic methods.

The invention further provides an article of manufacture and kit containing materials useful for neutralization of oral anticoagulants, particularly direct thrombin inhibitors. The article of manufacture comprises a container with a label. Suitable containers include, for example, bottles, vials, and test tubes. The containers may be formed from a variety of materials such as glass, metal, plastic or combinations thereof. The container holds a pharmaceutical composition comprising the antibody described herein or dabigatran, dabigatran etexilate, a prodrug of dabigatran or a pharmaceutically acceptable salt thereof. The active agent in the pharmaceutical composition is the particular antibody or dabigatran, dabigatran etexilate, a prodrug of dabigatran or a pharmaceutically acceptable salt thereof. The label on the container of the antibody indicates that the pharmaceutical composition is used for neutralizing or partially neutralizing dabigatran, dabigatran etexilate, a prodrug of dabigatran or a pharmaceutically acceptable salt thereof in vivo.

The kit of the invention comprises one or more of the containers described above. It may further include other materials desirable from a commercial and user standpoint, including other buffers, diluents, filters, needles, syringes, and package inserts with instructions for use.

In one embodiment of the invention, the kit comprises an antibody of any one the antibodies described herein or a pharmaceutical composition thereof. For example, the kit may comprise (1) any one the antibodies described herein or a pharmaceutical composition thereof, (2) a container and (3) a label.

In another embodiment, the kit comprises an antibody of any one the antibodies described herein or a pharmaceutical composition thereof, and dabigatran, dabigatran etexilate, a prodrug of dabigatran or a pharmaceutically acceptable salt thereof. The form of dabigatran, dabigatran etexilate, a prodrug of dabigatran or a pharmaceutically acceptable salt thereof may be in the form of a solid, liquid or gel. In a preferred embodiment, the pharmaceutically acceptable salt of dabigatran etexilate is a mesylate salt. In yet another preferred embodiment, the strength per dosage unit of the dabigatran, dabigatran etexilate, prodrug of dabigatran or pharmaceutically acceptable salt thereof is between about 50 mg and about 400 mg, about 75 mg and about 300 mg, about 75 mg and 150 mg, or about 110 mg and about 150 mg, given once-a-day (QD) or twice-a-day (BID). For example, the kit may comprise (1) any one the antibodies described herein or a pharmaceutical composition thereof, (2) a pharmaceutical composition of dabigatran, dabigatran etexilate, a prodrug of dabigatran or a pharmaceutically acceptable salt thereof, (3) a container and (4) a label.

In an alternate embodiment, the kit comprises (1) a first pharmaceutical composition comprising dabigatran, dabigatran etexilate, a prodrug of dabigatran or a pharmaceutically acceptable salt thereof, (2) a second pharmaceutical composition comprising any one the antibodies described herein or combination thereof, (3) instructions for separate administration of said first and second pharmaceutical compositions to a patient, wherein said first and second pharmaceutical compositions are contained in separate containers and said second pharmaceutical composition is administered to a patient requiring neutralization or partial neutralization of dabigatran or 1-O-acylglucuronide of dabigatran.

The invention also provides a diagnostic method to neutralize or partially neutralize dabigatran or 1-O-acylglucuronide of dabigatran in a patient being treated with dabigatran, dabigatran etexilate, a prodrug of dabigatran or a pharmaceutically acceptable salt thereof, comprising administering any one of the antibodies described herein, a combination thereof or a pharmaceutical composition thereof. Specifically, the invention provides a method for neutralizing or partially neutralizing dabigatran or 1-O-acylglucuronide of dabigatran in a patient comprising the steps of (a) confirming that a patient was being treated with dabigatran, dabigatran etexilate, a prodrug of dabigatran or a pharmaceutically acceptable salt thereof, and the amount that was taken by the patient; (b) neutralizing dabigatran or 1-O-acylglucuronide with any one of the antibodies described herein or combination thereof prior to performing a clotting or coagulation test or assay wherein dabigatran or the 1-O-acylglucuronide of dabigatran would interfere with the accurate read out of the test or assay results; (c) performing the clotting or coagulation test or assay on a sample taken from the patient to determine the level of clot formation without dabigatran or 1-O-acylglucuronide of dabigatran present; and (d) adjusting an amount of dabigatran, dabigatran etexilate, a prodrug of dabigatran or a pharmaceutically acceptable salt thereof administered to the patient in order to achieve the appropriate balance between clot formation and degradation in a patient. The molar ratio of antibody to dabigatran or 1-O-acylglucuronide of dabigatran is in the molar ratio of between 0.1 and 100, preferably between 0.1 and 10. The accurate read out of the test or assay result may be an accurate read out of fibrinogen levels, activated protein C resistance or related tests.

EXAMPLES

1. Production and Characterization of Anti-Dabigatran Antibodies and Fabs

Table 1 comprises the sequences of representative compounds of the invention as well as reference compounds used in the examples. All compounds can be manufactured by standard methods.

Fab compound FAB 5C/18 comprises HCVH5C (SEQ ID NO: 12) as heavy chain and LCVK18 (SEQ ID NO: 14) as light chain. A compound of that structure has been disclosed in international patent application WO 2012/130834 (named VH5c/Vk18 therein) and can be manufactured as described therein.

Fab compound FAB 5C/21 comprises HCVH5C (SEQ ID NO: 12) as heavy chain and LCVK21 (SEQ ID NO: 15) as light chain. A compound of that structure has been disclosed in international patent application WO 2012/130834 (named VH5c/Vk21 therein) and can be manufactured as described therein.

Fab compound FAB6 comprises heavy chain complementary determining regions (CDRs) CDR1 of SEQ ID NO: 1, CDR2 of SEQ ID NO: 2, and CDR3 of SEQ ID NO: 4, respectively. FAB6 comprises light chain complementary determining regions (CDRs) CDR1 of SEQ ID NO: 5, CDR2 of SEQ ID NO: 6, and CDR3 of SEQ ID NO: 7, respectively. Fab compound FAB6 comprises VHFAB6 (SEQ ID NO: 9) as heavy chain variable region and VK18 (SEQ ID NO: 10) as light chain variable region. Fab compound FAB6 comprises HCFAB6 (SEQ ID NO: 13) as heavy chain and LCVK18 (SEQ ID NO: 14) as light chain.

Fab compound ENG 15/18 comprises ENGVH15 (SEQ ID NO: 16) as heavy chain and ENGVK18 (SEQ ID NO: 17) as light chain. A compound of that structure has been described in international patent application WO 2011/089183 and can be manufactured as described therein.

In Table 1, the letters "CDR" denote a complementarity determining region, "VH" denotes the variable region of a heavy chain, "VK" denotes the variable region of a kappa light chain, "LC" denotes the light chain of an antibody molecule, and "HC" denotes the heavy chain of an antibody molecule. For example, "VHCDR1 5C" denotes the first CDR (CDR1) of the variable domain of the heavy chain termed 5C, and "VH5C" denotes the variable region of the heavy chain termed 5C.

TABLE 1

| SEQ ID NO | Designation | Sequence |
|---|---|---|
| 1 | VHCDR1 5C | GYTFTDYYMH |
| 2 | VHCDR2 5C | ETNPRNGGTTYNEKFKG |
| 3 | VHCDR3 5C | GTSGYDYFDY |
| 4 | VHCDR3 FAB6 | GTSGWDYFDY |
| 5 | VKCDR118 | RSSQSIVHSDGNIYLE |
| 6 | VKCDR218 | KVSYRFS |
| 7 | VKCDR318 | FQASHVPYT |
| 8 | VH5C | QVQLVQSGAE VKKPGASVKV SCKASGYTFT DYYMHWVRQA PGQGLEWMGE TNPRNGGTTY NEKFKGKATM TRDTSTSTAY MELSSLRSED TAVYYCTIGT SGYDYFDYWG QGTLVTVSS |
| 9 | VHFAB6 | QVQLVQSGAE VKKPGASVKV SCKASGYTFT DYYMHWVRQA PGQGLEWMGE TNPRNGGTTY NEKFKGKATM TRDTSTSTAY MELSSLRSED TAVYYCTIGT SGWDYFDYWG QGTLVTVSS |

TABLE 1-continued

| SEQ ID NO | Designation | Sequence |
|---|---|---|
| 10 | VK18 | DIVMTQTPLS LSVTPGQPAS ISCRSSQSIV HSDGNIYLEW YLQKPGQSPK LLIYKVSYRF SGVPDRFSGS GSGTDFTLKI SRVEAEDVGV YYCFQASHVP YTFGQGTKLE IK |
| 11 | VK21 | DIVMTQTPLS LSVTPGQPAS ISCRSSQSIV HSDGNIYLEW YLQKPGQSPK LLIYKVSYRF SGVPDRFSGS GSGTGFTLKI SRVEAEDVGV YYCFQASHVP YTFGGGTKLE IK |
| 12 | HCVH5C | QVQLVQSGAE VKKPGASVKV SCKASGYTFT DYYMHWVRQA PGQGLEWMGE TNPRNGGTTY NEKFKGKATM TRDTSTSTAY MELSSLRSED TAVYYCTIGT SGYDYFDYWG QGTLVTVSSA STKGPSVFPL APSSKSTSGG TAALGCLVKD YFPEPVTVSW NSGALTSGVH TFPAVLQSSG LYSLSSVVTV PSSSLGTQTY ICNVNHKPSN TKVDKKVEPK SC |
| 13 | HCFAB6 | QVQLVQSGAE VKKPGASVKV SCKASGYTFT DYYMHWVRQA PGQGLEWMGE TNPRNGGTTY NEKFKGKATM TRDTSTSTAY MELSSLRSED TAVYYCTIGT SGWDYFDYWG QGTLVTVSSA STKGPSVFPL APSSKSTSGG TAALGCLVKD YFPEPVTVSW NSGALTSGVH TFPAVLQSSG LYSLSSVVTV PSSSLGTQTY ICNVNHKPSN TKVDKKVEPK SC |
| 14 | LCVK18 | DIVMTQTPLS LSVTPGQPAS ISCRSSQSIV HSDGNIYLEW YLQKPGQSPK LLIYKVSYRF SGVPDRFSGS GSGTDFTLKI SRVEAEDVGV YYCFQASHVP YTFGQGTKLE IKRTVAAPSV FIFPPSDEQL KSGTASVVCL LNNFYPREAK VQWKVDNALQ SGNSQESVTE QDSKDSTYSL SSTLTLSKAD YEKHKVYACE VTHQGLSSPV TKSFNRGEC |
| 15 | LCVK21 | DIVMTQTPLS LSVTPGQPAS ISCRSSQSIV HSDGNIYLEW YLQKPGQSPK LLIYKVSYRF SGVPDRFSGS GSGTGFTLKI SRVEAEDVGV YYCFQASHVP YTFGGGTKLE IKRTVAAPSV FIFPPSDEQL KSGTASVVCL LNNFYPREAK VQWKVDNALQ SGNSQESVTE QDSKDSTYSL SSTLTLSKAD YEKHKVYACE VTHQGLSSPV TKSFNRGEC |
| 16 | ENGVH15 | QVQLQESGPG LVKPSETLSL TCTVSGFSLT SYIVDWIRQP PGKGLEWIGV IWAGGSTGYN SALRSRVSIT KDTSKNQFSL KLSSVTAADT AVYYCASAAY YSYYNYDGFA YWGQGTLVTV SSASTKGPSV FPLAPSSKST SGGTAALGCL VKDYFPEPVT VSWNSGALTS GVHTFPAVLQ SSGLYSLSSV VTVPSSSLGT QTYICNVNHK PSNTKVDKKV EPKSC |
| 17 | ENGVK18 | DVVMTQSPLS LPVTLGQPAS ISCKSSQSLL YTDGKTYLYW FLQRPGQSPR RLIYLVSKLD SGVPDRFSGS GSGTDFTLKI SRVEAEDVGV YYCLQSTHFP HTFGGGTKVE IKRTVAAPSV FIFPPSDEQL KSGTASVVCL LNNFYPREAK VQWKVDNALQ SGNSQESVTE QDSKDSTYSL SSTLTLSKAD YEKHKVYACE VTHQGLSSPV TKSFNRGEC |

2. Thrombin Clotting Time Assay

Briefly, human plasma is obtained by taking whole blood into 3.13% sodium citrate. This is then centrifuged to obtain platelet free plasma and transferred to a separate tube and frozen until required on the day of the assay. Plasma is thawed at 37° C. on the day of the assay.

The thrombin clotting time determination is performed as follows. First thrombin is diluted to manufacturer's specification (3 IU/mL thrombin) in the buffer provided (Dade Behring Test kit) and prewarmed to 37° C. It is used within 2 hrs of being prepared. All assays were performed on a commercially available CL4 clotting machine (Behnk Electronics, Norderstadt, Germany). Fifty μL of plasma is pipetted into provided cuvettes with a magnetic stirrer and allowed to stir for 2 min in the well preheated to 37° C. in the CL4 machine. At this point 100 μL of the thrombin solution is added and the time required for the plasma sample to clot is recorded automatically by the CL4. Dabigatran is preincubated for 5 min in plasma in the provided cuvettes, before adding thrombin and starting the measurement. If antibody is also tested (up 50 μL of stock solution), there is a further 5 minute incubation at 37° C. before beginning clotting (i.e. 10 min total incubation with dabigatran, 5 min total incubation with antibody and then clotting is initiated with thrombin).

TABLE 2

Thrombin Time Assay, IC50 values. Data represented as the mean of quadruplicate determinations.

| Fab | TT assay $IC_{50}$/nM |
|---|---|
| ENG 15/18 | 2.5 |
| FAB 5C/18 | 4.6 |
| FAB 5C/21 | 3.6 |
| FAB6 | 4.2 |

3. Affinity Determinations (Kinexa Method)

The affinities of Fab and mouse-human chimeric antibodies were determined using KinExA® technology. A constant concentration of Fab or chimeric antibody was incubated with various concentrations of dabigatran until equilibrium was reached. After this incubation the concentration of free antibody was determined by capturing the antibody on Neutravidin beads coupled with a Biotin-conjugated dabigatran analog. The captured Fab was detected with an anti-human IgG (Fab specific) F(ab')2 fragment labeled with FITC. The captured chimeric antibodies were detected with an anti-human IgG conjugated with Cy5. The dissociation constants ($K_D$) were calculated using a 1:1 binding model.

To measure rate constants ($k_{on}$ and $k_{off}$) with the KinExA® instrument, the Kinetics Direct method was used. In this method, the binding partners are mixed in solution, and the concentration of free active binding sites is probed over time as active binding sites are depleted due to the formation of complexes. Data points are collected at specified time intervals and the signals are analyzed. In this way, $k_{on}$ is measured directly and the off-rate $k_{off}$ is calculated as $k_{off} = K_D \times k_{on}$.

TABLE 3

$K_D$ values of Fabs determined using KinExA ® technology.

| Fab | $K_D$ | N | $k_{on}$ (1/Ms) | $k_{off}$ (1/s) (calculated) | N |
|---|---|---|---|---|---|
| ENG 15/18 | 2 | 5 | 3.43E+05 | 7.27E−07 | 3 |
| FAB 5C/18 | 180 | 11 | 1.27E+06 | 2.29E−04 | 2 |
| FAB 5C/21 | 173 | 10 | 1.37E+06 | 2.37E−04 | 2 |
| FAB6 | 18 | 3 | 2.85E+06 | 5.13E−05 | 3 |

4. Fab/Dabigatran Co-Crystallization and Structural Analysis

The Fabs were concentrated to 10 mg/ml, mixed with a 2 molar excess of dabigatran and incubated for 1 h at 4° C. Complex and crystallization solution were mixed 1:1. The complex crystallizes in 25% PEG 1500, 0.1 M SPG buffer (pH7).

Datasets for all crystals were collected on the Swiss light Source beamline PXI-X06SA of the Paul Scherrer Institut. All datasets were processed with the autoPROC package (Vonrhein, C., Flensburg, C., Keller, P., Sharff, A., Smart, O., Paciorek, W., Womack, T. & Bricogne, G. (2011). Data processing and analysis with the autoPROC toolbox. Acta Cryst. D67, 293-302.).

Fab FAB 5C/21: Dabigatran crystals grew in space group P2₁2₁2₁ with unit cell dimensions a=59.97 Å, b=78.39 Å, c=87, 67 Å and diffract to 2.2 Å resolution. The complex structure was solved by molecular replacement with the program phaser (Collaborative Computational Project, number 4. 1994. "The CCP4 Suite: Programs for Protein Crystallography". Acta Cryst. D50, 760-763. Phaser crystallographic software. McCoy A J, Grosse-Kunstleve R W, Adams P D, Winn M D, Storoni L C, Read R J. J. Appl. Cryst. (2007). 40, 658-674.) using a homologous Fab structure (PDB-ID 1C1E) as the starting search model. Analysis of the electron density map showed clear electron density for dabigatran. The complete structure was improved with multiple rounds of model building with Coot and refinement with autoBUSTER (Coot: model-building tools for molecular graphics" Emsley P, Cowtan K Acta Crystallographica Section D-Biological Crystallography 60: 2126-2132 Part 12 Sp. Iss. 1 DEC 2004. Bricogne G., Blanc E., Brandi M., Flensburg C., Keller P., Paciorek W., Roversi P, Sharff A., Smart O. S., Vonrhein C., Womack T. O. (2011). BUSTER version 2.11.2. Cambridge, United Kingdom: Global Phasing Ltd).

Fab FAB 5C/18: Dabigatran crystals grew in space group P2₁ and P2₁2₁2₁, respectively. Crystals with space group P2₁ showed unit cell dimensions of a=51.81 Å, b=128.92 Å, c=60.26 Å and diffract to 1.9 Å resolution. Crystals with space group P2₁2₁2₁ showed unit cell dimensions of a=48.20 Å, b=59.74 Å, c=127.69 Å and diffract to 2.2 Å resolution. Both complex structures were solved by molecular replacement with the program phaser using the structure of Fab VH5C/VK21 as the starting search model. Analysis of the electron density maps showed clear electron density for dabigatran. The complete structures were improved with multiple rounds of model building with Coot and refinement with autoBUSTER.

5. In Silico Analysis of Spatial Aggregation Propensity (SAP)

The spatial aggregation propensities (SAP) for each atom and each residue was calculated as described in (Chennamsetty et. al., Proc Natl Acad Sci; 2009, 106(29), pg 11937-11942) with the exception that residue hydrophobicity parameters where taken from (Cowan and Whittaker, Pept Res; 1990, 3(2), pg 75-80). The Fv SAP is calculated as the sum over all positive residue SAP values in the variable domains of the antibody. The CDR SAP is calculated as the sum over all positive residue SAP values in the complementary determining regions of the antibody. Fv SAP and CDR SAP have been calculated for 850 different antibody structures from the protein data bank (PDB), yielding a mean ($\mu_{Fv}$ and $\mu_{CDR}$) and standard deviation values ($\sigma_{Fv}$ and $\sigma_{CDR}$) for both properties.

Z-scores for the Fv SAP and CDR SAP for the antibodies where then calculated according to
Z-score(Fv SAP)=(Fv SAP−$\mu_{Fv}$)/$\sigma_{Fv}$ and
Z-score(CDR SAP)=(CDR SAP−$\mu_{CDR}$)/$\sigma_{CDR}$.
Results (FIG. 11):
Humanized Fab 18/15:
  Z-score(Fv SAP)=1.06
  Z-score(CDR SAP)=1.00
Humanized Fab VH5C/VK18:
  Z-score(Fv SAP)=−0.61
  Z-score(CDR SAP)=−0.84
Humanized Fab VH5C/VK21:
  Z-score(Fv SAP)=−0.61
  Z-score(CDR SAP)=−0.78

We claim:

1. An antibody molecule against dabigatran comprising a heavy chain variable domain with a CDR1 of SEQ ID NO: 1, a CDR2 of SEQ ID NO: 2, and a CDR3 of SEQ ID NO: 4, and a light chain variable domain with a CDR1 of SEQ ID NO: 5, a CDR2 of SEQ ID NO: 6, and a CDR3 of SEQ ID NO: 7.

2. The antibody molecule of claim 1 comprising a heavy chain variable domain of SEQ ID NO: 9 and a light chain variable domain of SEQ ID No: 10, or comprising a heavy chain variable domain of SEQ ID NO: 9 and a light chain variable domain of SEQ ID No: 11.

3. The antibody molecule of claim 1 comprising a heavy chain of SEQ ID NO: 13 and a light chain of SEQ ID No: 14, or comprising a heavy chain of SEQ ID NO: 13 and a light chain of SEQ ID No: 15.

4. The antibody molecule of claim 3, consisting of a heavy chain of SEQ ID NO: 13 and a light chain of SEQ ID No: 14, or consisting of a heavy chain of SEQ ID NO: 13 and a light chain of SEQ ID No: 15.

5. The antibody molecule of claim wherein the antibody molecule is a monoclonal antibody, a human antibody, a humanized antibody, a chimeric antibody, a fragment of an antibody, a Fab, Fab', or F(ab')$_2$ fragment, a single chain antibody, a single chain variable fragment (scFv), a Small Modular Immunopharmaceutical (SMIP), or a diabody.

6. A kit comprising an antibody molecule of claim 1, or a pharmaceutical composition thereof.

7. A kit comprising:
   (a) an antibody molecule of claim 1, or a pharmaceutical composition thereof;
   (b) a container; and
   (c) a label.

8. A kit comprising an antibody molecule of claim 1, and dabigatran, dabigatran etexilate, a prodrug of dabigatran or a pharmaceutically acceptable salt thereof.

9. A method for treating a side effects of dabigatran therapy or of an overdosing event in anticoagulant therapy, comprising administering an effective amount of an antibody molecule of claim 1 to a patient in need thereof.

10. The method according to claim 9, wherein the side effect is a bleeding event.

11. A method of manufacturing an antibody molecule of claim 1, comprising:
    (a) providing a host cell comprising one or more nucleic acids encoding the antibody molecule in functional association with an expression control sequence,
    (b) cultivating the host cell, and
    (c) recovering the antibody molecule from the cell culture.

12. A method for neutralizing or partially neutralizing dabigatran or 1-O-acylglucuronide of dabigatran in a patient being treated with dabigatran, dabigatran etexilate, a prodrug of dabigatran or a pharmaceutically acceptable salt thereof, comprising administering an antibody molecule of claim 1, or a pharmaceutical composition thereof.

13. A method for neutralizing or partially neutralizing dabigatran or 1-O-acylglucuronide of dabigatran in a patient comprising:
    (a) confirming that a patient was being treated with dabigatran, dabigatran etexilate, a prodrug of dabigatran or a pharmaceutically acceptable salt thereof, and the amount that was taken by the patient;
    (b) neutralizing dabigatran or 1-O-acylglucuronide with an antibody molecule of claim 1 prior to performing a clotting or coagulation test or assay wherein dabigatran or the 1-O-acylglucuronide of dabigatran would interfere with the accurate read out of the test or assay results;
    (c) performing the clotting or coagulation test or assay on a sample taken from the patient to determine the level of clot formation without dabigatran or 1-O-acylglucuronide of dabigatran present; and
    (d) adjusting an amount of dabigatran, dabigatran etexilate, a prodrug of dabigatran or a pharmaceutically acceptable salt thereof administered to the patient in order to achieve the appropriate balance between clot formation and degradation in a patient.

14. A method for reducing the concentration of dabigatran or 1-O-acylglucuronide of dabigatran in plasma of a patient being treated with dabigatran, dabigatran etexilate, a prodrug of dabigatran or a pharmaceutically acceptable salt thereof, comprising the step of administering an antibody molecule of claim 1, or a pharmaceutical composition thereof, to the patient.

15. A method of reversal of the anticoagulant effect of dabigatran or 1-O-acylglucuronide of dabigatran in a patient being treated with dabigatran, dabigatran etexilate, a prodrug of dabigatran or a pharmaceutically acceptable salt thereof, wherein the patient either has major bleeding considered life-threatening or leading to hemodynamic compromise, or wherein the patient requires emergency medical procedures, comprising the step of administering an antibody molecule of claim 1, or a pharmaceutical composition thereof, to the patient.

16. A method for reversing or reducing the activity of dabigatran or 1-O-acylglucuronide of dabigatran in a patient experiencing bleeding or at risk for bleeding due to an impaired clotting ability or trauma, comprising the steps of:
    (a) determining the amount of dabigatran or 1-O-acylglucuronide of dabigatran present in the patient;
    (b) administering an effective amount of an antibody molecule of claim 1 to reverse or reduce the activity of dabigatran or 1-O-acylglucuronide of dabigatran determined in the patient; and
    (c) monitoring a thrombin clotting time of the patient to ensure a reversal or reduction in activity of dabigatran or 1-O-acylglucuronide of dabigatran has been reached.

* * * * *

SEQUENCE LISTING

<160> NUMBER OF SEQ ID NOS: 17

<210> SEQ ID NO 1
<211> LENGTH: 10
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 1

Gly Tyr Thr Phe Thr Asp Tyr Tyr Met His
1               5                   10

<210> SEQ ID NO 2
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Glu Thr Asn Pro Arg Asn Gly Gly Thr Thr Tyr Asn Glu Lys Phe Lys
1               5                   10                  15

Gly

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Thr Ser Gly Tyr Asp Tyr Phe Asp Tyr
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Thr Ser Gly Trp Asp Tyr Phe Asp Tyr
1               5                   10

<210> SEQ ID NO 5
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Arg Ser Ser Gln Ser Ile Val His Ser Asp Gly Asn Ile Tyr Leu Glu
1               5                   10                  15

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 6

Lys Val Ser Tyr Arg Phe Ser
1               5

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Phe Gln Ala Ser His Val Pro Tyr Thr
1               5

<210> SEQ ID NO 8
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met His Trp Val Arg Gln Ala Pro Gly Gln Gly Leu Glu Trp Met
        35                  40                  45

Gly Glu Thr Asn Pro Arg Asn Gly Gly Thr Thr Tyr Asn Glu Lys Phe
    50                  55                  60

Lys Gly Lys Ala Thr Met Thr Arg Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Ile Gly Thr Ser Gly Tyr Asp Tyr Phe Asp Tyr Trp Gly Gln Gly
            100                 105                 110

Thr Leu Val Thr Val Ser Ser
        115

<210> SEQ ID NO 9
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met His Trp Val Arg Gln Ala Pro Gly Gln Gly Leu Glu Trp Met
        35                  40                  45

Gly Glu Thr Asn Pro Arg Asn Gly Gly Thr Thr Tyr Asn Glu Lys Phe
    50                  55                  60

Lys Gly Lys Ala Thr Met Thr Arg Asp Thr Ser Thr Ser Thr Ala Tyr
65                  70                  75                  80

```
Met Glu Leu Ser Ser Leu Arg Ser Glu Asp Thr Ala Val Tyr Tyr Cys
                85                  90                  95

Thr Ile Gly Thr Ser Gly Trp Asp Tyr Phe Asp Tyr Trp Gly Gln Gly
            100                 105                 110

Thr Leu Val Thr Val Ser Ser
        115

<210> SEQ ID NO 10
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Ile Val His Ser
            20                  25                  30

Asp Gly Asn Ile Tyr Leu Glu Trp Tyr Leu Gln Lys Pro Gly Gln Ser
        35                  40                  45

Pro Lys Leu Leu Ile Tyr Lys Val Ser Tyr Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Ala
                85                  90                  95

Ser His Val Pro Tyr Thr Phe Gly Gln Gly Thr Lys Leu Glu Ile Lys
            100                 105                 110

<210> SEQ ID NO 11
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Ile Val His Ser
            20                  25                  30

Asp Gly Asn Ile Tyr Leu Glu Trp Tyr Leu Gln Lys Pro Gly Gln Ser
        35                  40                  45

Pro Lys Leu Leu Ile Tyr Lys Val Ser Tyr Arg Phe Ser Gly Val Pro
    50                  55                  60

Asp Arg Phe Ser Gly Ser Gly Ser Gly Thr Gly Phe Thr Leu Lys Ile
65                  70                  75                  80

Ser Arg Val Glu Ala Glu Asp Val Gly Val Tyr Tyr Cys Phe Gln Ala
                85                  90                  95

Ser His Val Pro Tyr Thr Phe Gly Gly Gly Thr Lys Leu Glu Ile Lys
            100                 105                 110

<210> SEQ ID NO 12
<211> LENGTH: 222
<212> TYPE: PRT
<213> ORGANISM: Artificial Sequence
```

<220> FEATURE:
<223> OTHER INFORMATION: Description of Artificial Sequence: Synthetic
      polypeptide

<400> SEQUENCE: 12

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met His Trp Val Arg Gln Ala Pro Gly Gln Gly Leu Glu Trp Met
        35                  40                  45

Gly Glu Thr Asn Pro Arg Asn Gly Gly Thr Thr Tyr Asn Glu Lys Phe
    50                  55                  60

Lys Gly Lys Ala Thr Met Thr Arg Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Ile Gly Thr Ser Gly Tyr Asp Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys
    210                 215                 220

<210> SEQ ID NO 13
<211> LENGTH: 222
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met His Trp Val Arg Gln Ala Pro Gly Gln Gly Leu Glu Trp Met
        35                  40                  45

Gly Glu Thr Asn Pro Arg Asn Gly Gly Thr Thr Tyr Asn Glu Lys Phe
    50                  55                  60

Lys Gly Lys Ala Thr Met Thr Arg Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Ile Gly Thr Ser Gly Trp Asp Tyr Phe Asp Tyr Trp Gly Gln Gly
            100                 105                 110

```
Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys
210                 215                 220

<210> SEQ ID NO 14
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Ile Val His Ser
            20                  25                  30

Asp Gly Asn Ile Tyr Leu Glu Trp Tyr Leu Gln Lys Pro Gly Gln Ser
        35                  40                  45

Pro Lys Leu Leu Ile Tyr Lys Val Ser Tyr Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Ala
                85                  90                  95

Ser His Val Pro Tyr Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 15
<211> LENGTH: 219
<212> TYPE: PRT
<213> ORGANISM: Artificial Sequence
```

<220> FEATURE:
<223> OTHER INFORMATION: Description of Artificial Sequence: Synthetic
      polypeptide

<400> SEQUENCE: 15

Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Ile Val His Ser
            20                  25                  30

Asp Gly Asn Ile Tyr Leu Glu Trp Tyr Leu Gln Lys Pro Gly Gln Ser
        35                  40                  45

Pro Lys Leu Leu Ile Tyr Lys Val Ser Tyr Arg Phe Ser Gly Val Pro
    50                  55                  60

Asp Arg Phe Ser Gly Ser Gly Ser Gly Thr Gly Phe Thr Leu Lys Ile
65                  70                  75                  80

Ser Arg Val Glu Ala Glu Asp Val Gly Val Tyr Tyr Cys Phe Gln Ala
                85                  90                  95

Ser His Val Pro Tyr Thr Phe Gly Gly Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 16
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

Ile Val Asp Trp Ile Arg Gln Pro Pro Gly Lys Gly Leu Glu Trp Ile
        35                  40                  45

Gly Val Ile Trp Ala Gly Gly Ser Thr Gly Tyr Asn Ser Ala Leu Arg
    50                  55                  60

Ser Arg Val Ser Ile Thr Lys Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

```
Ser Ala Ala Tyr Tyr Ser Tyr Tyr Asn Tyr Asp Gly Phe Ala Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
            165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
            195                 200                 205

His Lys Pro Ser Asn Thr Lys Val Asp Lys Lys Val Glu Pro Lys Ser
            210                 215                 220

Cys
225

<210> SEQ ID NO 17
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Asp Val Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Tyr Thr
            20                  25                  30

Asp Gly Lys Thr Tyr Leu Tyr Trp Phe Leu Gln Arg Pro Gly Gln Ser
        35                  40                  45

Pro Arg Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Leu Gln Ser
                85                  90                  95

Thr His Phe Pro His Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
            165                 170                 175

Thr Tyr Ser Leu Ser Ser Thr Leu Thr Leu Ser Lys Ala Asp Tyr Glu
            180                 185                 190
```

-continued

```
Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```